United States Patent
Tekeli et al.

(10) Patent No.: US 12,295,873 B2
(45) Date of Patent: May 13, 2025

(54) URINARY SYSTEM MAKING THE INVOLUNTARY EXCRETION OCCURING AFTER COLOSTOMY, ILEOSTOMY AND UROSTOMY VOLUNTARY

(71) Applicant: LEGNA MEDIKAL TEKNOLOJI SANAYI VE TICARET ANONIM SIRKETI, Istanbul (TR)

(72) Inventors: Onur Tekeli, Istanbul (TR); Kenan Kursun, Istanbul (TR); Ozgur Er, Antalya (TR)

(73) Assignee: LEGNA MEDIKAL TEKNOLOJI SANAYI VE TICARET ANONIM SIRKETI, Istanbul (TR)

( * ) Notice: Subject to any disclaimer, the term of this patent is extended or adjusted under 35 U.S.C. 154(b) by 426 days.

(21) Appl. No.: 17/909,768

(22) PCT Filed: Mar. 16, 2020

(86) PCT No.: PCT/TR2020/050206
§ 371 (c)(1),
(2) Date: Sep. 7, 2022

(87) PCT Pub. No.: WO2021/188061
PCT Pub. Date: Sep. 23, 2021

(65) Prior Publication Data
US 2023/0099115 A1    Mar. 30, 2023

(51) Int. Cl.
*A61F 5/449* (2006.01)
*A61F 5/44* (2006.01)
*A61F 5/445* (2006.01)

(52) U.S. Cl.
CPC .......... *A61F 5/4405* (2013.01); *A61F 5/4404* (2013.01); *A61F 5/449* (2013.01)

(58) Field of Classification Search
CPC ....... A61F 5/4405; A61F 5/4404; A61F 5/449
See application file for complete search history.

(56) References Cited

U.S. PATENT DOCUMENTS 2,341,984 A * 2/1944 Graves .................... A61F 5/445
                                                  604/332
2,510,766 A * 6/1950 Surface ................... A61F 5/445
                                                  600/32

(Continued)

FOREIGN PATENT DOCUMENTS

EP        2642958 B1    10/2017
TR    201909670 A2      7/2019

(Continued)

OTHER PUBLICATIONS

Ineke Claessens, et al., The Ostomy Life Study: the everyday challenges faced by people living with a stoma in a snapshot, Gastrointestinal Nursing, 2015, pp. 18-25, vol. 13, No. 5.

*Primary Examiner* — Guy K Townsend
(74) *Attorney, Agent, or Firm* — Bayramoglu Law Offices LLC

(57) ABSTRACT

A urinary system is used to excrete the contents of the large intestine, small intestine and urinary bladder through the stoma after colostomy, ileostomy and urostomy and makes the involuntary excretion occurring in the stoma voluntary and is connected to the bottom adapter adhering to the skin such that it will isolate the stoma in the excretory region of the user's abdominal wall.

17 Claims, 3 Drawing Sheets

(56) References Cited

U.S. PATENT DOCUMENTS

| | | | | |
|---|---|---|---|---|
| 3,374,856 | A * | 3/1968 | Wirt | F24F 13/24 |
| | | | | 138/144 |
| 3,447,533 | A * | 6/1969 | Spicer | A61F 5/445 |
| | | | | 600/32 |
| 3,906,951 | A * | 9/1975 | Chen | A61L 28/008 |
| | | | | 604/336 |
| 4,137,918 | A * | 2/1979 | Bogert | A61F 5/445 |
| | | | | 604/328 |
| 4,338,937 | A * | 7/1982 | Lerman | A61F 2/0018 |
| | | | | 600/32 |
| 4,634,421 | A * | 1/1987 | Hegemann | A61F 2/0009 |
| | | | | 604/277 |
| 4,662,890 | A * | 5/1987 | Burton | A61F 5/445 |
| | | | | 604/277 |
| 4,721,508 | A * | 1/1988 | Burton | A61F 5/445 |
| | | | | 604/277 |
| 4,786,283 | A * | 11/1988 | Andersson | A61F 5/448 |
| | | | | 604/338 |
| 4,804,375 | A * | 2/1989 | Robertson | A61F 2/0013 |
| | | | | 604/323 |
| 4,854,316 | A * | 8/1989 | Davis | A61F 2/0063 |
| | | | | 604/8 |
| 4,941,869 | A * | 7/1990 | D'Amico | A61F 5/445 |
| | | | | 604/277 |
| 5,269,774 | A * | 12/1993 | Gray | A61F 5/449 |
| | | | | 604/338 |
| 5,658,266 | A * | 8/1997 | Colacello | A61F 5/441 |
| | | | | 604/277 |
| 5,771,590 | A * | 6/1998 | Colacello | A61F 5/445 |
| | | | | 30/360 |
| 5,891,113 | A * | 4/1999 | Quinn | A61J 15/0061 |
| | | | | 604/905 |
| 6,033,390 | A * | 3/2000 | von Dyck | A61F 5/445 |
| | | | | 604/174 |
| 6,050,982 | A * | 4/2000 | Wheeler | A61F 5/445 |
| | | | | 600/32 |
| 6,485,476 | B1 * | 11/2002 | von Dyck | A61F 5/441 |
| | | | | 604/332 |
| 6,595,971 | B1 * | 7/2003 | von Dyck | A61M 3/0202 |
| | | | | 604/334 |
| 6,689,111 | B2 * | 2/2004 | Mulhauser | A61F 5/445 |
| | | | | 604/332 |
| 7,001,367 | B2 * | 2/2006 | Arkinstall | A61F 5/445 |
| | | | | 604/337 |
| 7,765,007 | B2 * | 7/2010 | Martino | A61N 1/36007 |
| | | | | 607/40 |
| 8,105,299 | B2 * | 1/2012 | Shah | A61F 5/445 |
| | | | | 604/338 |
| 8,167,859 | B2 * | 5/2012 | Shah | B29C 66/54 |
| | | | | 604/382 |
| 8,529,429 | B2 * | 9/2013 | Gobel | A61F 2/0013 |
| | | | | 600/32 |
| 8,821,465 | B2 * | 9/2014 | Hanuka | A61F 5/4407 |
| | | | | 604/333 |
| 8,864,729 | B2 * | 10/2014 | Hanuka | A61F 5/443 |
| | | | | 604/334 |
| 8,998,862 | B2 * | 4/2015 | Hanuka | A61F 5/4405 |
| | | | | 604/318 |
| 9,186,233 | B2 * | 11/2015 | Göbel | A61F 2/0013 |
| 10,166,138 | B2 * | 1/2019 | Cline | A61F 5/445 |
| 10,537,461 | B2 * | 1/2020 | Hanuka | A61F 5/441 |
| 11,166,838 | B2 * | 11/2021 | Cline | A61F 5/445 |
| 2002/0077611 | A1 * | 6/2002 | von Dyck | A61F 5/442 |
| | | | | 604/332 |
| 2003/0220621 | A1 * | 11/2003 | Arkinstall | A61F 5/445 |
| | | | | 604/335 |
| 2007/0142780 | A1 * | 6/2007 | Van Lue | A61B 17/3462 |
| | | | | 604/167.01 |
| 2008/0262449 | A1 * | 10/2008 | Shah | B29C 66/1122 |
| | | | | 604/338 |
| 2010/0069859 | A1 * | 3/2010 | Weig | A61F 2/0027 |
| | | | | 604/335 |
| 2010/0174253 | A1 * | 7/2010 | Cline | A61F 5/445 |
| | | | | 604/328 |
| 2010/0241092 | A1 * | 9/2010 | Nguyen-Demary | A61F 5/4407 |
| | | | | 604/336 |
| 2011/0015475 | A1 * | 1/2011 | Hanuka | A61F 2/04 |
| | | | | 600/32 |
| 2011/0040231 | A1 * | 2/2011 | Gregory | A61F 5/445 |
| | | | | 604/8 |
| 2011/0106032 | A1 * | 5/2011 | Kratky | A61F 5/445 |
| | | | | 604/337 |
| 2011/0306823 | A1 * | 12/2011 | Gobel | A61F 2/0013 |
| | | | | 600/32 |
| 2012/0136324 | A1 * | 5/2012 | Hanuka | A61F 5/441 |
| | | | | 604/318 |
| 2013/0035654 | A1 * | 2/2013 | Friske | A61F 5/445 |
| | | | | 604/344 |
| 2013/0060213 | A1 * | 3/2013 | Hanuka | A61F 5/441 |
| | | | | 604/344 |
| 2013/0079738 | A1 * | 3/2013 | Hanuka | A61F 5/445 |
| | | | | 604/335 |
| 2019/0133813 | A1 * | 5/2019 | Cline | A61F 5/445 |
| 2022/0054297 | A1 * | 2/2022 | Cline | A61F 5/445 |

FOREIGN PATENT DOCUMENTS

| | | | | |
|---|---|---|---|---|
| WO | WO-9960959 | A1 * | 12/1999 | A61F 5/443 |
| WO | WO-2011091801 | A1 * | 8/2011 | A61F 5/445 |

* cited by examiner

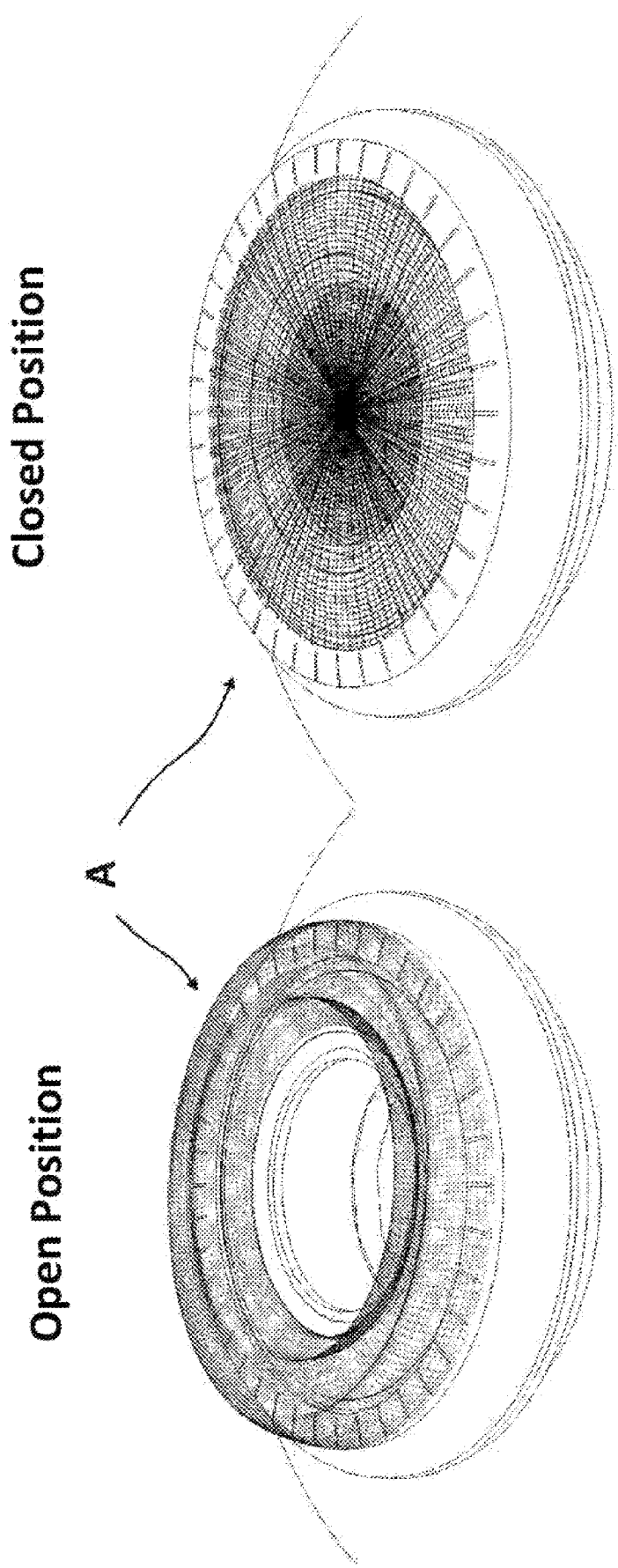

URINARY SYSTEM MAKING THE INVOLUNTARY EXCRETION OCCURING AFTER COLOSTOMY, ILEOSTOMY AND UROSTOMY VOLUNTARY

CROSS REFERENCE TO THE RELATED APPLICATIONS

This application is the national phase entry of International Application No. PCT/TR2020/050206, filed on Mar. 16, 2020, the entire contents of which are incorporated herein by reference.

TECHNICAL FIELD

The invention relates to a urinary system consisting of mechanical and electronical elements, which is used to excrete the contents of the large intestine, small intestine and urinary bladder through the stoma after colostomy, ileostomy and urostomy and makes the involuntary excretion occurring in the stoma voluntary.

BACKGROUND

In the state of the art, excreting the contents of the large intestine, small intestine and urinary bladder through the stoma after colostomy, ileostomy and urostomy occurs into the ostomy bag involuntarily at anytime, anywhere and at any circumstances. In the environment, the occurrence of situations such as noise and smell during excretion is also prevented. At the same time, bowel gas discharge is constantly occurring. At the same time, the ostomy bag is filled due to the continuous discharge and bowel gas discharge, and the person has to control the ostomy bag by stopping the everyday activities or waking up at night.

The scientific article entitled "The Ostomy Life Study: The everyday challenges faced by people living with a stoma in a snapshot", of which the link is given below and published on July-2015 at the scientific publication named "Gastrointestinal Nursing" describes the ostomy bags applications and the disadvantages experienced in these applications in a detailed way.

The related article detail can be accessed via the web link "https://www.researchgate.net/publication/281389672_The_Ostomy_Life_Study_The_everyday_challenges_faced_by_people_living_with_a_stoma_in_a_snapshot?enrich Id=rgreq-991ee2195c65fd90006468bc6b15ee31-XXX&enrichSource=Y292ZXJQYWdlOzI4MTM4OTY3MjtBUzo2MTEzNDgxNzg zMDA5MjhAMTUyMjc2ODE3MjAyMg %3D %3D&el=1_x_2&_esc=publicationCoverPdf".

In the patent research performed, no patent similar to the system subject to the invention was found. Nevertheless, some patents prepared in the same technical field are referred to below. One of them is TR2019/09670 numbered patent application. The related invention relates to a proximal distal stoma set that provides GIS (gastrointestinal system) integrity by delivering safely intestinal contents coming from the proximal bowel extension through the distal extension. Said set is similar to the existing bag structures that are especially applied to new-born babies having bowel problems. It does not contain any electronic component.

European Patent Application publication number EP2642958B1 relates to a stoma leakage collecting device, a connecting plate and the mounted state and connecting plate of said device. The invention is directed to patients having the stoma or reservoir surgery. However, it does not bear a resemblance to the system subject of the invention.

SUMMARY

Based on the state of the art, the main object of the invention is to develop a urinary system consisting of mechanical and electronical elements, which is used to excrete the contents of the large intestine, small intestine and urinary bladder through the stoma after colostomy, ileostomy and urostomy and makes the involuntary excretion occurring in the stoma voluntary.

Another object of the invention is to prevent the undesired situations such as bowel gas discharge, smell and noise while making the excretion voluntary.

BRIEF DESCRIPTION OF THE DRAWINGS

FIG. 3 is the perspective view of the urinary system according to the invention while in an assembled and open condition.

FIG. 4 is the perspective view of the urinary system according to the invention while in an assembled and open condition.

DESCRIPTION OF THE REFERENCED

Figure 1:
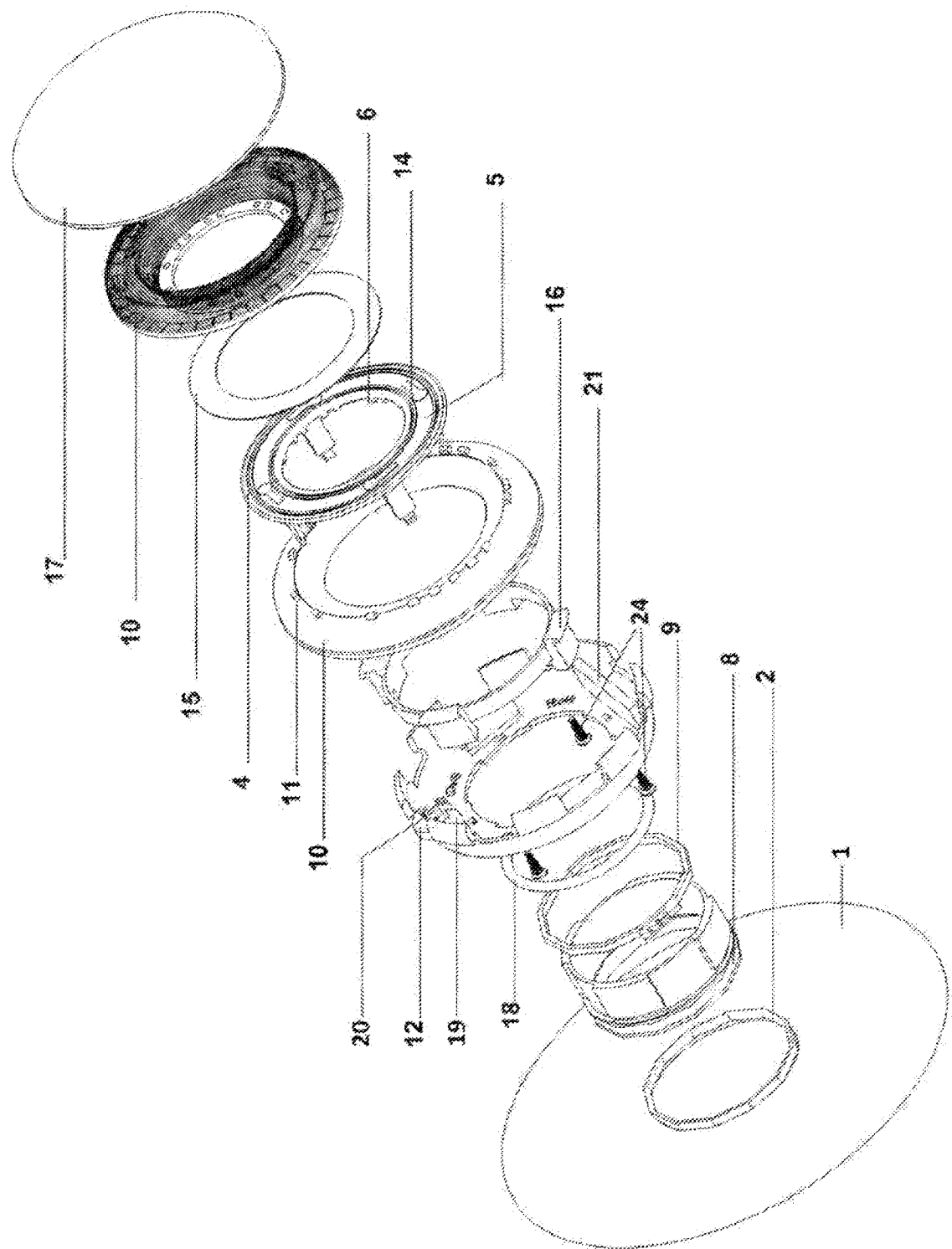
FIG. 1 is the perspective view of the urinary system according to the invention in a disassembled condition.
Figure 2:
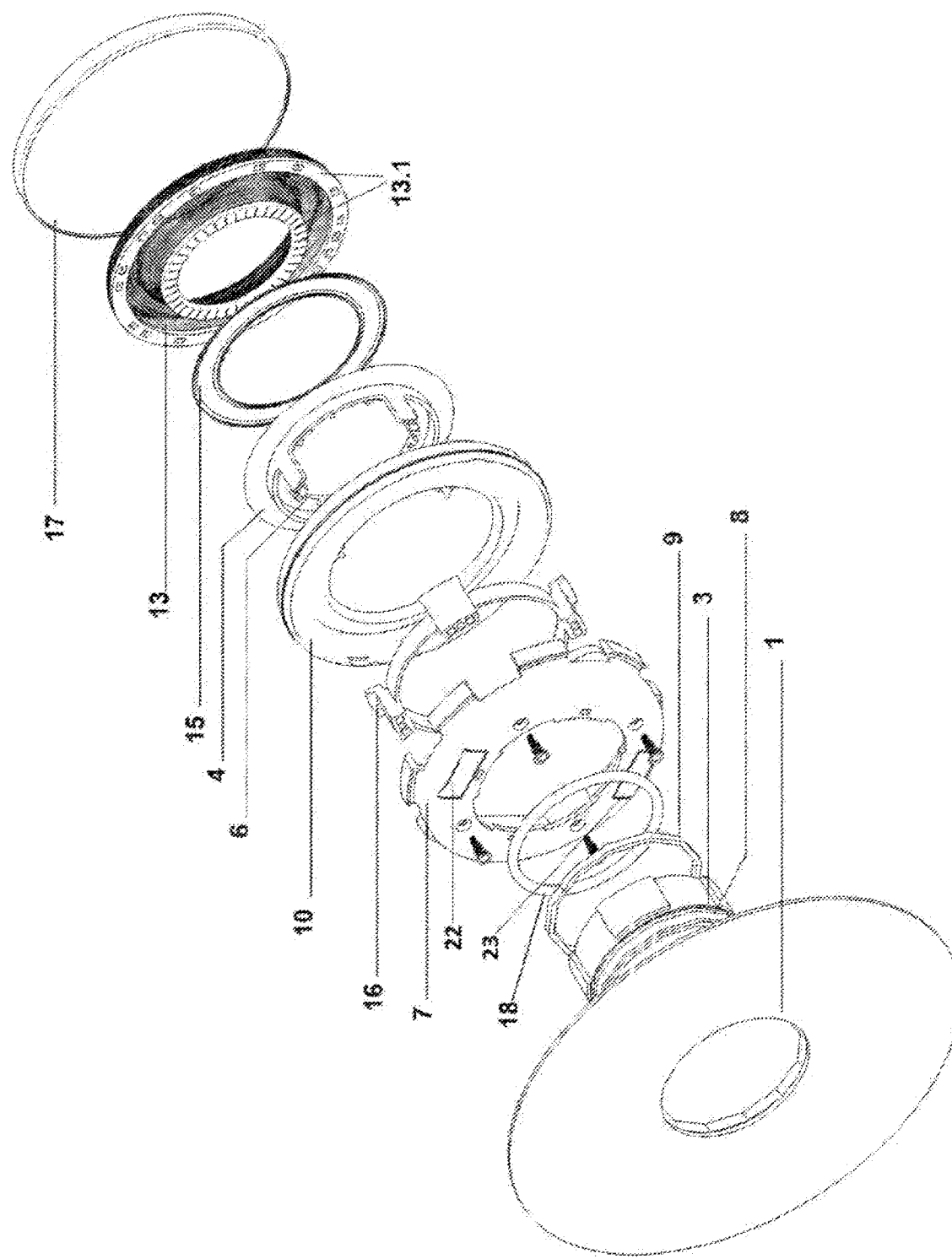
FIG. 2 is the perspective view of the urinary system according to the invention in a disassembled condition from a different angle.

B. Urinary system
25. Bottom adapter
26. Polygonal semi-elastic orifice structure
27. Fastening channels
28. Inner body
29. Sensor bearings
30. Inner orifice fastening structure
31. Side outer shell
32. Polygonal bedding orifice structure
33. Clamp
34. Axial rotation piece
35. Outer orifice fastening structure
36. Closed position and emergency discharge projection
37. Elastic cylinder tube
37.1. Thickened structures
38. Pressure sensors
39. Pressure rings
40. Inner bedding piece
41. Upper cover
42. Inner orifice seal
43. Vibration motor
44. Emergency motor
45. Circuit board
46. External battery
47. Covered battery bearing
48. Connection element

DETAILED DESCRIPTION OF THE EMBODIMENTS

The invention relates to a urinary system (A) consisting of mechanical and electronical elements, which is used to excrete the contents of the large intestine, small intestine and urinary bladder through the stoma after colostomy, ileostomy and urostomy and makes the involuntary excretion occurring in the stoma voluntary.

The bottom adapter (1) is the elastic polymer structure adhering to the skin such that it will isolate the stoma in the excretory region of the user's abdominal wall.

Polygonal semi-elastic orifice structure (2) is the structure that is used in order to prevent turning and leakage after the system is fastened to the bottom adapter (1), is semi-elastic in the polygonal form and integrated with the rubber surface of the bottom adapter (1).

The fastening channels (3) allow the inner body (4) to be fastened to the bottom adapter (1) by sliding and also allow the location where it is fastened to be determined.

Thanks to the projections on it, the inner body (4) is a cylindrical structure that allows the independent system to be combined and separated with the bottom adapter (1) by user by making spiral sliding with the help of the channels located on the orifice part of the bottom adapter (1) and thus working with the bottom adapter (1) and at the same time serves as the main body for other product components.

The sensor bearing (5) is a circular-shaped recessed slot formed on the inner body (4) that ensures the pressure sensors (14) located on the inner body (4) to remain stationary.

The inner orifice fastening structure (6) is on the inner perimeter of the inner body (4) and enables the inner orifice of the elastic cylinder tube (13) to be fastened to the inner body (4).

The side outer shell (7) is the piece that is combined from the outside by telescoping with the inner body (4) and shapes the gaps and spaces required for the internal components of the product together with the inner body (4).

Polygonal bedding orifice structure (8) is the structure that fits internally the polygonal semi-elastic orifice structure (2) on the bottom adapter (1) of the system and prevents its uncontrolled rotation by being fastened with the clamp (9).

After fitting internally the polygonal semi-elastic orifice structure (2) on the bottom adapter (1) of the system, the clamp (9) is used that tightens the two polygonal structures and provides sealing.

The axial return piece (10) is a piece that is fastened by bedding the rotation axis of it with the inner body (4) and the side outer shell (7) pieces, which can be rotated freely in both opposite directions on only one axis, of which orifice is fastened by the user to the inner wall of the inner body (4), which plays a key role in rotating the other orifice while one mouth of the elastic cylinder tube (13) is stationary and thus opening and closing the system by creating a buckling.

The outer orifice fastening structure (11) is the structure which is on the axial return piece (10) and to which the outer orifice of the elastic cylinder tube (13) can be fastened.

Closed position and emergency discharge projection (12) are spring-loaded projection present in the side outer shell (7), that are mechanically released by the emergency motor (20) in the need of emergency discharge when the system is in the closed position, and which allow the system to open suddenly thanks to the elastic resistance of the elastic cylinder tube (13) in the opposite direction.

The elastic cylinder tube (13) is an elastic piece with steady linear flexibility, which does not have solid, liquid and gas permeability and has thickened structures (13.1) in both orifices of it, one of which is enabled to be fastened to the inner body (4) and the other to the axial rotation piece (10).

The pressure sensors (14) are a number of identical receivers placed on the upper part of the inner body (4) and measuring the pressure force created by the elastic cylinder tube (13) on itself.

The pressure ring (15) is a hollow circular structure which is made of semi-elastic polymer and has projections positioned such that each one of the pressure sensors (14) are positioned on the top of it. The pressure sensors (14) and the elastic cylinder tube (13) play an important role in measuring the desired force ranges by regulating the force relations between them.

The inner bedding piece (16) is the piece providing the basic bedding for the rotation of the axial rotation piece (10). It is mounted to the side outer shell (7) with the help of a sufficient number of connection element (24) from the bottom.

The upper cover (17) is the piece that provides the closed elastic cylinder tube (13) to be closed for both security and visual purposes in closed position, in cases where the product opened and closed manually by the user is not used.

The inner orifice seal (18) is the piece that provides sealing by squeezing between these two when the inner body (4) is connected to the bottom adapter (1).

The vibration motor (19) is the motor that allows the product to give a warning to the user about the need for defecation by direct vibration.

In case of emergency discharge requirement in the intestine, if the user is unable to provide it manually, the emergency motor (20) is the motor, which allows the axial rotation piece (10) to turn somewhat in the opposite direction by making a quarter turn in the specified direction and in this way the system to be opened suddenly thanks to elastic resistance of the elastic cylinder tube (13) in the opposite direction.

The circuit board (21) used in the system according to the invention is the circuit element that regulates the relationships between the sensors, motors and warning types to be made to the user in various ways.

The external battery (22) is an external and rechargeable battery that provides the necessary energy to all elements operating on electrical energy in the system.

The covered battery bearing (23) is the piece that enables the external battery (22) to be protected and fastened.

The Working Principle of the Invention After the bottom adapter (1) is adhered on the surface of the abdominal cavity such that it will isolate the stoma, integration of the urinary system (A) into the body is provided. The system, which is completed by mounting the inner body (4), the side outer shell (7), the axial rotation piece (10) and the inner bedding piece (16) with each other and containing a structure that includes all other pieces, is now ready to be mounted on the bottom adapter (1). Here, the clamp (9) minimizes "directional defects that may occur in the axis of rotation" by allowing an external bedding on itself such that it will support bedding that can be made one-way on the inner body (4) for the axial rotation piece (10). The projections on the inner circumference of the side outer shell (7) to make the system to be attached to the bottom adapter (1) are turned at an angle of 45 degrees after following a compulsory linear path in the bottom adapter fastening channels (3) and the system is fastened to the bottom adapter (1) in the desired position. At this stage, the rotation of the system in the opposite direction is prevented by inserting the polygonal bedding orifice structure (8) into the polygonal semi-elastic orifice structure (2) on the bottom adapter (1) and the fastening process is completed.

After the fastening process is completed, the inner orifice of the elastic cylinder tube (13) is fastened to the inner orifice fastening structure (6) located in the inner body (4). Then, the outer orifice of the elastic cylinder tube (13) is fastened to the outer orifice fastening structure (11) located on the axial rotation piece (10). Now, the product is ready for use. The product works mainly by enabling the other orifice the elastic cylinder tube (13) fastened by the user to the inner wall of the inner body (4) to rotate, while one orifice of it is stationary by performing the free rotation of the axial rotation piece (10) both in two opposite directions on only one axis and thus by enabling the system to be opened and closed by creating a buckling.

Another important factor that enables the excretion to be made voluntary that will be performed as a result of the operation of the system. The sensor bearings (5) on the inner body (4) are used to place 4 pressure sensors (14). The pressure ring (15) having an elastic polymer structure is mounted on these pressure sensors (14) again at the production stage, which is placed during the factory assembly of the system according to the invention. In the phase where the elastic cylinder tube (13) provides full closure by being buckled, the maximum force is applied on the pressure ring (15). The pressure ring (15) also transmits this force to the pressure sensors (14). The force information coming from the pressure sensors (14) is read and interpreted by the circuit board (21). The excretion force, such as defecation etc. to be applied outward by the intestine will push the barrier formed by the buckling of the elastic cylinder tube (13) outward and the force on the pressure sensors (14) will decrease in direct proportion to this force applied from the inside out. The circuit board (21) will interpret these force changes in accordance with the defined software directives and send the user a warning on various digital platforms, primarily the vibration of the system. Creating vibration of the system will be provided by the vibration motor (19). As a result of the warnings coming, the user may use a suitable place like toilet, bathroom, etc. in order to perform excretion voluntarily, by opening the upper cover (17), rotating the axial rotation piece (10) in the specified direction and releasing it. By this means, the excretion path will be opened and discharge will take place.

After the discharge is completed, the user will close the axial rotation piece (10) by rotating it in the opposite direction and clean the outer part of the barrier formed by the buckling of the elastic cylinder tube (13) by using one of the cleaning methods after toilet that people use in their normal life. The entire process will be completed by the user closing the upper cover (17) again.

However, due to various negative external factors such as fainting, panic attack, forced sleep, the user may not be able to perform discharge process despite all warnings. In this case, the health of the user who cannot perform discharge is compromised. In such a scenario, the value ranges defined on the circuit board (21) are interpreted and the emergency engine (20) is activated. If the emergency motor (20) receives the necessary directive, it pushes back the closed position and emergency discharge projection (12) located in the side outer shell (7) by making quarter turn. The system is released and hence the elastic structure is autogenously buckled by using elastic force caused by buckling in the opposite direction and it passes from the closed position to the flat and open position. In this way, the buckling barrier opens and excretion occurs involuntarily. The electronic part of the system consists of a number of pressure sensors (14), vibration motors (19), emergency motors (20) and circuit boards (21) and the energy required for them is provided by the external battery (22) or batteries installed in the covered battery bearing (23).

What is claimed is:

1. A urinary system used to excrete contents of a large intestine, small intestine and urinary bladder through a stoma after colostomy, ileostomy and urostomy, making an involuntary excretion occurring in a stoma voluntary and connected to a bottom adapter adhering to a skin such that the urinary system isolates the stoma in an excretory region of a user's abdominal wall, wherein the urinary system comprises;

an inner body, wherein the inner body is locked by combining with the bottom adapter by making spiral sliding and hence allowing an independent system operating freely to be combined and separated with the bottom adapter by user and serving as a main body for other product components at a same time;

a side outer shell, wherein the side outer shell is combined from an outside by telescoping with the inner body and shapes gaps and spaces required for internal components of the urinary system together with the inner body;

an axial rotation piece, wherein the axial rotation piece is fastened by bedding a rotation axis of the axial rotation piece with the inner body and the side outer shell, which can be rotated freely in both opposite directions on only one axis, of which orifice is fastened by the user to an inner wall of the inner body;

an elastic cylinder tube, wherein the elastic cylinder tube has thickened structures in both orifices of the elastic cylinder tube, one of the thickened structures is enabled to be fastened to the inner body and the other to the axial rotation piece; and an inner bedding piece, wherein the inner bedding piece provides a main inner bedding for a rotation of the axial rotation piece and is mounted on the side outer shell.

2. The urinary system according to claim 1, further comprising fastening channels, wherein the fastening channels allow the inner body to be fastened to the bottom adapter by sliding and also allow a location where it the inner body is fastened to be determined.

3. The urinary system according to claim 1, further comprising a polygonal semi-elastic orifice structure, wherein the polygonal semi-elastic orifice structure is integrated with a rubber surface of the bottom adapter, wherein the rubber surface of the bottom adapter adheres to the body, and the polygonal semi-elastic orifice structure is used to prevent turning and leakage after the urinary system is fastened to the bottom adapter.

4. The urinary system according to claim 1, further comprising an inner orifice fastening structure, wherein the inner orifice fastening structure is on an inner perimeter of the inner body and enables an inner orifice of the elastic cylinder tube to be fastened to the inner body.

5. The urinary system according to claim 1, further comprising a polygonal bedding orifice structure, wherein the polygonal bedding orifice structure fits internally a polygonal semi-elastic orifice structure on the bottom adapter of the urinary system and prevents an uncontrolled rotation by being fastened with a clamp.

6. The urinary system according to claim 1, further comprising a clamp, wherein after the clamp is fitted internally the polygonal semi-elastic orifice structure on the bottom adapter of the urinary system, the clamp tightens two polygonal structures and provides sealing by being fastened.

7. The urinary system according to claim 1, further comprising an outer orifice fastening structure, wherein the outer orifice fastening structure is on the axial rotation piece and an outer orifice of the elastic cylinder tube is fastened in the outer orifice fastening structure.

8. The urinary system according to claim 1, further comprising a closed position and an emergency discharge projection, wherein the closed position and the emergency discharge projection are spring-loaded projection present in the side outer shell, the closed position and the emergency discharge projection are mechanically released by an emergency motor in a need of emergency discharge when the urinary system is in the closed position, and the closed position and the emergency discharge projection allow the urinary system to open suddenly thanks to an elastic resistance of the elastic cylinder tube in an opposite direction.

9. The urinary system according to claim 1, further comprising a plurality of pressure sensors, wherein the plurality of pressure sensors are placed on an upper part of the inner body and measure a pressure force created by the elastic cylinder tube on the inner body.

10. The urinary system according to claim 1, further comprising a pressure ring, wherein the pressure ring is used to measure desired force ranges by regulating force relations between the pressure ring and the elastic cylinder tube, and the pressure ring is made of semi-elastic polymer and positioned such that each of pressure sensors is positioned on a top of the pressure ring.

11. The urinary system according to claim 1, further comprising an upper cover, wherein the upper cover provides the elastic cylinder tube to be closed for both security and visual purposes in a closed position, in cases where a product opened and closed manually by the user is not used.

12. The urinary system according to claim 1, further comprising an inner orifice seal, wherein the inner orifice seal provides sealing by squeezing between these two when the inner body is connected to the bottom adapter.

13. The urinary system according to claim 1, further comprising a vibration motor, wherein the vibration motor allows a product to give a warning to the user about a need for defecation by direct vibration.

14. The urinary system according to claim 1, further comprising an emergency motor, wherein in case of an emergency discharge requirement in an intestine, if the user is unable to provide the emergency motor manually, the emergency motor allows the axial rotation piece to be released such that the axial rotation piece is turned in an opposite direction by turning in a specified direction and the urinary system is opened suddenly thanks to elastic resistance of the elastic cylinder tube in the opposite direction.

15. The urinary system according to claim 1, further comprising a circuit board, wherein the circuit board regulates relationships between sensors, motors and warning types to be made to the user in various ways.

16. The urinary system according to claim 1, further comprising a rechargeable external battery, wherein the rechargeable external battery provides a necessary energy to all elements operating on electrical energy in the urinary system.

17. The urinary system according to claim 1, further comprising a covered battery bearing, wherein the covered battery bearing enables an external battery to be protected and fastened.

* * * * *